US006551800B1

(12) United States Patent
Bulla, Jr. et al.

(10) Patent No.: US 6,551,800 B1
(45) Date of Patent: Apr. 22, 2003

(54) RECOMBINANT MATERIALS FOR PRODUCTION OF A PROTEIN TOXIC TO FIRE ANTS

(75) Inventors: Lee A. Bulla, Jr., Tioga, TX (US); Mehmet Candas, Dallas, TX (US)

(73) Assignee: The Board of Regents, The University Texas System, Austin, TX (US)

(*) Notice: Subject to any disclaimer, the term of this patent is extended or adjusted under 35 U.S.C. 154(b) by 0 days.

(21) Appl. No.: 09/696,348

(22) Filed: Oct. 24, 2000

Related U.S. Application Data

(60) Provisional application No. 60/161,495, filed on Oct. 26, 1999.

(51) Int. Cl.$^7$ .............. C12P 21/04; C12N 1/08; C12N 1/20; C07K 14/06; C07H 21/04
(52) U.S. Cl. .......... 435/71.1; 435/6; 435/69.1; 435/91.1; 435/270; 435/471; 435/485; 435/252.3; 435/252.31; 435/320.1; 530/324; 530/350; 536/23.1; 536/23.71
(58) Field of Search .............. 435/6, 91.1, 270, 435/252.3, 69.1, 71.1, 471, 485, 252.31, 320.1; 536/23.1, 23.71; 530/350, 324

(56) References Cited

U.S. PATENT DOCUMENTS

| 5,260,058 | A | | 11/1993 | Payne et al. |
| 5,268,297 | A | | 12/1993 | Payne et al. |
| 5,338,544 | A | | 8/1994 | Donovan |
| 5,596,071 | A | | 1/1997 | Payne et al. |
| 5,659,123 | A | * | 8/1997 | Van Rie et al. ............. 800/205 |
| 5,824,792 | A | | 10/1998 | Payne et al. |

FOREIGN PATENT DOCUMENTS

EP 0 213 818 8/1986

OTHER PUBLICATIONS

Bulla et al., Crit. Rev. Microbiol. (1980) 8:147–204.
Gill et al., Ann. Rev. Entomol. (1992) 37:615.
Höfte and Whitley, Microbiol. Rev. (1989) 53:242.
Schnepf et al., Microbiol. Mol. Biol. Rev. (1998) 62(3):775.
Sekar et al., PNAS USA (1987) 84(20):7036–7040.

* cited by examiner

Primary Examiner—B. L. Sisson
(74) Attorney, Agent, or Firm—Morrison & Foerster, LLP

(57) ABSTRACT

A nucleic acid derived from *Bacillus thuringiensis* contains a nucleotide sequence that encodes a polypeptide demonstrated to be toxic to fire ants.

14 Claims, 7 Drawing Sheets

* 200 µg/ml per bioassay; $LC_{50}$ not determined.

Figure 3

|          | M | PURIFIED-PAPAIN ACTIVATED TOXIN |
|----------|---|---------------------------------|
| 116 →    |   |                                 |
| 97 →     |   |                                 |
| 84 →     |   |                                 |
| 66 →     |   |                                 |
| 55 →     |   |                                 |
| 45 →     |   |                                 |

Figure 4A

```
ATGAATCCGAACAATCGAAGTGAACATGATACAATAAAAACTACTGAAAATAATGAGGTG    60
CCAACTAACCATGTTCAATATCCTTTAGCGGAAACTCCAAATCCAACACTAGAAGATTTA   120
AATTATAAAGAGTTTTTAAGAATGACTGCAGATAATAATACGGAAGCACTAGATAGCTCT   180
ACAACAAAAGATGTCATTCAAAAAGGCATTTCCGTAGTAGGTGATCTCCTAGGCGTAGTA   240
GGTTTCCCGTTTGGTGGAGCGCTTGTTTCGTTTTATACAAACTTTTTAAATACTATTTGG   300
CCAAGTGAAGACCCGTGGAAGGCTTTTATGGAACAAGTAGAAGCATTGATGGATCAGAAA   360
ATAGCTGATTATGCAAAAAATAAAGCTCTTGCAGAGTTACAGGGCCTTCAAAATAATGTC   420
GAAGATTATGTGAGTGCATTGAGTTCATGGCAAAAAAATCCTGTGAGTTCACGAAATCCA   480
CATAGCCAGGGGCGGATAAGAGAGCTGTTTTCTCAAGCAGAAAGTCATTTCGTAATTCA   540
ATGCCTTCGTTTGCAATTTCTGGATACGAGGTTCTATTTCTAACAACATATGCACAAGCT   600
GCCAACACACATTTATTTTTACTAAAAGACGCTCAAATTTATGGAGAAGAATGGGGATAC   660
AAAAAGAAGATATTGCTGAATTTTTAAAAAGACAACTAAAACTTACCCAGGAATATACT   720
GACCATTTTGTTCAATGGTATTATGTTGGATTAGATAAAATTAGAGGTTCATTCTATGAA   780
TCTTGGGTAAACTTTAACCGTTATCGCAGAGAGATGACATTAACAGTATTAGATTTAATT   840
GCACTATTTCCATTGTATGATGTTCGGCTATACCCAAAAGAAGTTAAAACCGAATTAACA   900
AGAGACGTTTTAACAGATCCAATTGTCGGAGTCAACAACCTTAGGGGCTATGGAACAACC   960
TTCTCTAATATAGAAAATTATATTCGAAAACCACATCTATTTGACTATCTGCATAGAATT  1020
CAATTTCACACGCGGTTCCAACCAGGATATTATGGAAATGACTCTTTCAATTATTGGTCC  1080
GGTAATTATGTTTCAACTAGACCAAGCATAGGATCAAATGATATAATCACATCTCCATTC  1140
TATGGAAATAAATCCAGTGAACCTGTACAAAATTTAGGATTTAATGGAGAAAAAGTCTAT  1200
AGAGCCGTAGCAAATACAAATCTTGCGGTCTGGCCGTCCGCTGTAAATTCAGGTGTAACA  1260
AAAGTGAAATTTAGCCAATATAATGATCAAACAGATGAAGCAAGTACACAAACGTCGGAC  1320
TCAAAAAGAAATGTTGGCGCGGTCAGCTGGGATTCTATCGATCAATTGCCTCCAGAAGCA  1380
ACAGATGAACCTCTAGAAAAGGGATATAGCCATCAACTCAATTATGTAATGTGCTTTTA  1440
ATGCAGGGTAGTAGAGGAACAATCCCAGTGTTAACTTGGACACATAAAAGTGTAGACTTT  1500
TTTAACATGATTGATTCGAAAAAAATTACACAACTTCCGTTAGTAAAGGCATATAAGTTA  1560
CAATCTGGTGCTTCCGTTGTCGCAGGTCCTAGGTTTACAGGAGGAGATATCATTCAATGC  1620
ACAGAAAATGGAAGTGCGGCAACTATTTACGTTACACCGGATGTGTCGTACTCTCAAAAA  1680
TATCGAGCTAGAATTCATTATGCTTCTACATCTCAGATAACATTTACACTCAGTTTAGAC  1740
GGGGCACCATTTAATCAATACTATTTCGATAAAACGATAAATAAAGGAGACACATTAACG  1800
TATAATTCATTTAATTTAGCAAGTTTCAGCACACCATTCGAATTATCAGGGAATAACTTA  1860
CAAATAGGCGTCACAGGATTAAGTGCTGGAGATAAAGTTTATATAGACAAAATTGAATTT  1920
ATTCCAGTGAATTAAA  1936
```

Figure 6

```
MNPNNRSEHD TIKTTENNEV PTNHVQYPLA ETPNPTLEDL NYKEFLRMTA 50
           ↓         ↓
DNNTEALDSS TTKDVIQKGI SVVGDLLGVV GFPFGGALVS FYTNFLNTIW 100
PSEDPWKAFM EQVEALMDQK IADYAKNKAL AELQGLQNNV EDYVSALSSW 150
QKNPVSSRNP HSQGRIRELF SQAESHFRNS MPSFAISGYE VLFLTTYAQA 200
ANTHLFLLKD AQIYGEEWGY KKEDIAEFLK RQLKLTQEYT DHFVQWYYVG 250
LDKIRGSFYE SWVNFNRYRR EMTLTVLDLI ALFPLYDVRL YPKEVKTELT 300
RDVLTDPIVG VNNLRGYGTT FSNIENYIRK PHLFDYLHRI QFHTRFQPGY 350
YGNDSFNYWS GNYVSTRPSI GSNDIITSPF YGNKSSEPVQ NLGFNGEKVY 400
RAVANTNLAV WPSAVNSGVT KVKFSQYNDQ TDEASTQTSD SKRNVGAVSW    450
DSIDQLPPEA TDEPLEKGYS HQLNYVMCFL MQGSRGTIPV LTWTHKSVDF 500
FNMIDSKKIT QLPLVKAYKL QSGASVVAGP RFTGGDIIQC TENGSAATIY 550
VTPDVSYSQK YRARIHYAST SQITFTLSLD GAPFNQYYFD KTINKGDTLT 600
YNSFNLASFS TPFELSGNNL QIGVTGLSAG DKVYIDKIEF IPVN        644
```

Figure 7

RECOMBINANT MATERIALS FOR PRODUCTION OF A PROTEIN TOXIC TO FIRE ANTS

CROSS-REFERENCES TO RELATED APPLICATIONS

This Application for Patent claims the benefit of priority from, and hereby incorporates by reference the entire disclosure of, co-pending U.S. Provisional Application for Patent Ser. No. 60/161,495, filed Oct. 26, 1999.

TECHNICAL FIELD OF THE INVENTION

This invention relates to methods and compositions for controlling populations of Hymenopteran insect pests in the Formicidae (ant) family using a novel *Bacillus thuringiensis* ("PT") toxin and preparation. In particular, the invention relates to effective methods of controlling populations of various fire ants of the family Solenopsis using a BT toxin effective in killing fire ants, and a novel strain of BT producing such toxin.

BACKGROUND OF THE INVENTION

Without limiting the scope of the invention, its background is described in connection with uses of *Bacillus thuringiensis* toxins as fire ant biocidal agents as an example. The imported fire ant, *Solenopsis invicta*, is an introduced species that arrived in Mobile, Ala. from South America around the 1930s. The imported fire ant has spread rapidly across the southern United States and continues to expand into areas of North America with mild climates and adequate moisture and food.

The imported fire ant is an agriculturally and medically important pest harmful to domestic animals, wildlife and humans. Fire ants particularly threaten obligate ground dwelling species and young animals of all species. The imported fire ant is thought to be responsible for the decline of several native species. Proliferation of the imported fire ant has been largely unchecked due to the absence of predators, pathogens and parasites that control its numbers in its native environment. The fire ant typically causes painful stings in humans and more severe reactions may occur in allergic individuals. High densities of fire ants have been responsible for damage to roads, pastures, and electrical and mechanical equipment. The recent appearance of multiple queen colonies has made control of fire ant populations even more difficult. An effective compound and method for control of fire ant populations that is safe to users and consumers is urgently needed.

Past attempts at fire ant control have involved the highly toxic chlorinated hydrocarbons heptachlor, dieldrin, and Mirex. The EPA has outlawed the use of these highly toxic albeit relatively effective compounds for all but exceptional applications. The most commonly used modern control methods used include the chemicals hydramethylnon, avermectin, and the synthetic insect growth regulator fenoxycarb. These compounds must be regularly reapplied and have not been able to significantly impact severe fire ant infestations or to control further spread. The search for control methods is now being conducted in the areas of sterile insect release and the introduction of natural enemies, both of which are only potential solutions with uncertain outcomes.

*Bacillus thuringiensis* ("BT") is the genus and species of a large number of strains of gram-positive, spore-forming bacteria which, under certain conditions, form a parasporal crystal comprised of insecticidal protein toxin (Bulla, et al., *Crit. Rev. Microbiol.*, 8:147–204, (1980); Höfte and Whitely, *Microbiol Rev* (1989) 53:242, (1989). The toxin itself is a glycoprotein product of cry genes ("Cry" is used to denote the protein; "cry" is used to denote the gene) as described by Höfte (Id.). Because the effects of the various Cry proteins are mediated by binding to unique receptors, the species specificity of a given BT toxin is typically quite limited as exemplified by the original classification proposed by Höfte (Id.): CryI (Lepidopteran specific); CryII (Lepidopteran and Dipteran specific); CryIII (Coleoptera specific); and CryIV (Diptera specific). The BT toxins function in the brush border of insect midgut epithelial cells and, although highly insecticidal to certain insects, are non-toxic to other organisms lacking toxin binding receptors (Gill, S. S. et al. *Ann. Rev. Entomol* (1992) 37:615).

Keen interest in BT toxins over the last 30 years has resulted in the isolation of more than 100 different BT crystal protein genes and the development of bioinsecticides for the control of insect species in the orders Lepidoptera, Diptera, Coleoptera, Hymenoptera, Homoptera, Orthoptera and Mallophaga and against nematodes, mites and protozoa (Schnepf et al., *Microbiol. Mol. Biol. Rev.* (1998) 62(3):775). BT toxin in various forms now accounts for 90% of the world sales of non-chemical insecticides.

U.S. Pat. Nos. 5,260,058, 5,268,297, 5,596,071 and 5,824,792, disclose processes and compositions for controlling pharoah ants (*Monomorium pharaonis*) using toxin containing bacterial cells of various BT strains. Although these toxins are alleged to be effective against all Hymenoptera and all ants, no testing beyond the pharoah ant was performed. Further, the protoxins of this invention were much larger (120–140 kD) than that described herein.

SUMMARY OF THE INVENTION

Prior to this invention, no BT toxins have been reported that are known to be effective in controlling fire ants, nor are any BT toxins commercially available for this indication. What is needed is a biocidal composition that is effective in controlling populations of the fire ant, yet is not toxic to non-insect organisms. Such a biocide would have broad applicability including the agricultural, domestic, environmental and biomedical arenas. For this reason a BT toxin effective in killing fire ants would be particularly desirable.

Fire ants are omnivorous, although a large portion of their diet comprises invertebrates which the fire ants sting and kill. They also feed on dead animal and plant tissues, seeds, developing and ripe fruits, and are attracted to honeydew and sap flows. They are attracted to sugars, certain amino acids, ions in solution, and to some oils containing polyunsaturated fatty acids in these food sources.

Worker ants can only consume liquid foods, and nearly half of the resources that are returned to the nest are in the form of liquids. Liquids consumed and stored by the foraging workers are fed to other workers through trophallaxis. Once the worker arrives back at the colony, the oils are slowly transferred to nurses and from the nurses to larvae. Soluble sugars in addition to some soluble protein and amino acid mixtures are strongly attractive and encourage trophallaxis among workers. This both dilutes the solution and reduces the speed of movement of these nutrients to larvae.

Undissolved solids greater than 0.88 microns are screened from the liquid in the pharynx of the worker fire ant and cannot be ingested by the worker ants. The solids accumulate in the buccal region as pellets and are later expelled to feed fourth-instar stage larvae, which are able to consume particles as large as 45 microns. Because solid food may be used by the mature larvae but not the workers, solids move from the field to these larvae more quickly and directly than liquid foods. After processing by the fourth instar larvae, previously solid foods can be utilized by the queen and young larvae through trophallaxis. As it is desirable that worker ants transport poisons back to the colony and distribute the poison throughout the colony, consideration to the favored foods of fire ants together with the physical size of the poison may influence the efficacy of treatment modalities.

The present invention provides a BT protein that is active against members of the Formicidae family, in particular the imported fire ant, Solenopsis invicta, and related species. Generally, the invention provides BT preparations that are effective in reducing populations of fire ants and related species. The invention further provides novel B. thuringiensis strains that produce toxins effective against fire ants and related species. Effectiveness is defined as the ability to reduce the numbers of ants within a local fire ant population, typically a mound-type community, by killing immature and/or mature individuals within the population who are exposed to the toxin. Exposure may take the form of ingestion of the subject toxin either directly in a bait formulation or as expressed in a food source or by trophallaxis.

This invention provides biologically pure cultures of an isolated BT bacterial cell having the identifying characteristics of strain UTD-001 (NRRL No. B-30356).

In an alternate embodiment, the invention further provides recombinant DNA derived from the BT strain having the identifying characteristics of UTD-001 and encoding BT Cry toxin proteins. These characteristics include an approximately 73 kD wild type Cry protoxin protein that is activated on proteolytic processing to an approximately 67 kD toxin, has toxic activity against fire ants, has activity between pH 5–7, an SDS-PAGE profile substantially as shown in FIG. 2, and an arbitrary-primed PCR product profile substantially as shown in FIG. 3.

The DNA encoding BT Cry toxins may be isolated and cloned as recombinant DNA by the methods known in the art such as for example in the standard cloning manual of Sambrook, et al., Molecular Cloning: A Laboratory Manual (Cold Spring Harbor Laboratory, Cold Spring Harbor, N.Y. 2nd ed. 1989). The cry gene from UTD-001 has been cloned, and the sequences of the invention are identified as follows:

| SEQ ID NO: 1 | Nucleic acid sequence for the cry protoxin gene cloned from UTD-001. |
| SEQ ID NO: 2 | Amino acid sequence encoded by SEQ ID NO: 1 including active protein from residues 56 or 58 to 644. |
| SEQ ID NO: 3 | Forward primer cry3A-F used to clone SEQ ID NO: 1; ATGAATCCGAACAATCGAAG |
| SEQ ID NO: 4 | Reverse primer cry3A-R used to clone SEQ ID NO: 1; TTAATTCACTGGAATAAATTC. |

The invention further provides vectors for the cloning and expression of recombinant DNA encoding BT Cry protoxins or toxins that are toxic to fire ants. According to methods known in the art, the vectors may be adapted for expression of the Cry protoxin or toxin protein in various host organisms as desired. The invention contemplates the use of these expression vectors to produce novel host organisms which are engineered to express the encoded proteins either transiently, upon induction, or constitutively. Host organisms include those that are merely used as factories for the production of large quantities of toxin which is then purified and formulated into a bait. Alternatively, host organisms include organisms engineered to both express the protein and to serve as a food source for fire ants. Host organisms may include prokaryotic cells and eukaryotic cells and organisms such as for example, yeast, fungi, plants or animals.

The invention further provides purified Cry protoxins and toxins and compositions of these proteins that are active against Hymenoptera, Formicidae, and especially Solenopsis. In one embodiment, the Cry protoxin disclosed herein is characterized by a molecular weight of about 73 kD by SDS-PAGE, and 72.9 kD by calculation from the conceptually translated protein. The protoxin is putatively cleaved at residue 55 (between EA) by papain, and at residue 57 (between LD) by trypsin to produce an active protein. Thus, the protoxin is reduced to a toxin of about 67 kD by proteolytic digestion. However, it is expected that this cleavage site is somewhat flexible resulting in small variations in size of the active toxin. The novel Cry toxin of the present invention may also be described as a Cry3A-like toxin based on its close homology to the Cry3A toxin of Btt.

In one such embodiment, the Cry toxin is toxic to Formicidae, including Solenopsis invicta, S. richteri, S. xyloni, S. geminatam, S. geminata (aka Atta geminata Fabricius or S. geminata Mayr, S. japonica (aka S. fugax var. japonica), S. saevissima, S. orbuloides, S. punctaticeps, a variety of Solenopsis species identified by number, and related fire ant species. The invention provides methods for reducing ant populations by compositions containing Cry toxin or protoxin produced by BT strains having the identifying characteristics of UTD-001.

In yet another embodiment of the present invention, a biocide is produced by (a) propagating B. thuringiensis microorganisms having the identifying characteristics of strains UTD-001 under conditions wherein Cry protoxin is produced; (b) purifying the Cry protoxin; and (c) formulating the purified Cry protoxin into a biocide effective against ants. The Cry protoxin may be pre-activated by proteolytic digestion prior to formulating it into a bait, or may be produced directly in toxin form by the host organism.

In a further embodiment, the invention provides methods for isolating and cloning the BT toxin receptor of the imported fire ant and for using such receptor to engineer toxins with greater potency against the fire ant and for avoiding any resistance which may develop subsequent to the application of the present invention to fire ant populations.

BRIEF DESCRIPTION OF THE DRAWINGS

A more complete understanding of the method and apparatus of the present invention may be obtained by reference to the following Detailed Description when taken in conjunction with the accompanying Drawings wherein:

FIG. 3 shows a fire ant toxin assay where purified papain treated toxin is compared against purified toxin, crude spores & crystal toxin, and controls;

FIGS. 4A and 4B are the SDS-PAGE profiles of the activated toxin (4A) and crude spore and crystal toxin (4B) The 73 kD protoxin and 67 kD toxin are both seen in 4B. The molecular weight markers (kD) are also indicated;

FIG. 6 is the nucleotide sequence (SEQ ID NO: 1) of the Cry protoxin of UTD-001; and FIG. 7 is the amino acid sequence (SEQ ID NO: 2) of the Cry protoxin of UTD-001. The active toxin portion is in bold face. The arrow indicates putative cleavage sites for the protoxin.

DETAILED DESCRIPTION OF THE PRESENTLY PREFERRED EXEMPLARY EMBODIMENTS

Figure 1:
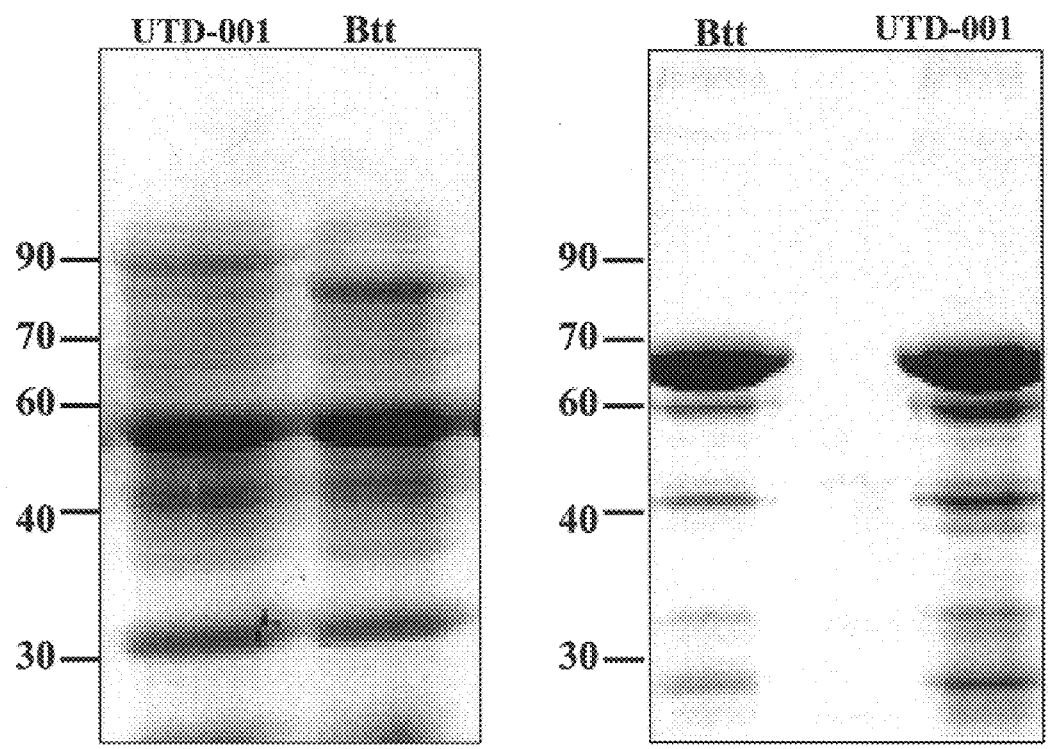
FIG. 1 is a Coomassie blue stained SDS-PAGE gel of the cytoplasmic proteins isolated from UTD-001 and a control species, B. thuringiensis, subs. tenebrionis (Btt). The left panel is proteins from vegetative cells, whereas the right panel is from sporulating cells. The patterns clearly demonstrate that the UTD-001 strain has a Cry toxin of approximately the same size (about 67 kD) as the Cry3A protein of Btt. Molecular weight size markers (kD) are also indicated.

The present invention will now be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Abbreviations and Definitions

The following abbreviations and definitions are used throughout this application: BT—*Bacillus thuringiensis* (*B. thuringiensis*); Btt—*Bacillus thuringiensis* subsp. *tenebrionis*; Cry toxin—toxin derived from parasporal crystalline protein; cry—the gene encoding Cry toxin; EDTA—disodium ethylenediaminetetraacetate, dehydrate; kD—kilodaltons; LB—Luria broth; $LC_{50}$—lethal concentration resulting in a 50% mortality; PMSF—phenylmethane sulfonyl fluoride; and SDS-PAGE—sodium dodecyl sulfate polyacryamide gel electrophoresis.

The term "x% homology" refers to the extent to which two nucleic acid or protein sequences are identical as determined by BLAST homology alignment as described by T. A. Tatusova & T. L. Madden (1999), "Blast 2 sequences—a new tool for comparing protein and nucleotide sequences," FEMS Microbiol Lett. 174:247–250 and using the following parameters: Program (blastn) or (blastp) as appropriate; matrix (OBLOSUM62), reward for match (1); penalty for mismatch (–2); open gap (5) and extension gap (2) penalties; gap x- drop off (50); Expect (10); word size (11); filter (off). An example of a web based two sequence alignment program using these parameters is found at www.ncbi.nlm.nih.gov/gorf/bl2.html. High stringency is defined as including a final wash of 0.2×SSC at a temperature of 60° C.

The present invention concerns a novel BT isolate and genes therefrom that encode a novel Hymenoptera-active protein. In particular, the toxins are active against the Formicidae and especially the Solenopsis. The novel BT isolate, known herein as *Bacillus thuringiensis* UTD-001 as well as protoxins and toxins from this isolate, may be used to control pests such as fire ants, carpenter ants, Argentine ants, and pharaoh ants.

The BT toxin gene from isolate UTD-001 has been cloned and sequenced and is presented in FIG. 6 (SEQ ID Nos.: 1 and 2). The coding region is from nucleotides 1 to end (1936). The protein in FIG. 7 is 644 amino acids, and includes an pro-region from amino acids 1 to 55 or 57 and an active region from amino acids 56 or 58 to the end. The pI of the protoxin is 5.67. The cry gene is 98% homologous to the cry3A gene of Btt, which appears to be its closest relative at this time.

The novel toxin disclosed herein is active against ants, especially fire ants. The present invention provides those of skill in the art with a Solenopsis-active toxin, methods for using the toxin, and gene that encodes the toxin. The gene or gene fragment that encodes the Solenopsis-active toxin may be cloned and the gene fragment encoding the toxin gene may be transferred to suitable hosts via a recombinant DNA vector.

Because the Cry toxins generally have a very broad range of species specificity, it is anticipated that the Cry toxins of the invention will have activity against other Hymenoptera. Species specificity studies will be performed to confirm this prediction.

Recombinant hosts for use as ant food sources comprising the Cry toxins of the invention may include a wide variety of microbial or plant hosts. Expression of the toxin gene results, directly or indirectly, in the production of the pesticide toxin. An important feature of this embodiment of the invention is that the toxin produced should not form a crystal within the host, as is the norm in BT, because fire ants filter out large particles, such as the crystal, while eating. Therefore, the host must not produce a crystal that is larger that the particle size that fire ants exclude during the eating process (e.g. 0.88 microns). Of course, the cry gene may be engineered to produce the active, soluble 67 kD form of the toxin which circumvents the size exclusion problem.

With suitable microbial hosts, e.g., Pseudomonas, the microbes may be applied to the situs of the pest, where they will proliferate and be ingested. The result is effective control of the fire ant. Factors that may be considered in selecting a host cell for *Bacillus thuringiensis* toxin production according to the present invention include: gene-host compatibility, ease of host transformation; availability of expression systems; efficiency of expression; stability of the toxin in the host; the presence of auxiliary genetic capabilities and whether the host is to function as a direct food source for the target insect, or merely function as a source of toxin. Other factors that may be considered include: pathogenicity of the host to animals and humans; ease of formulation and handling, economics, storage stability, and the like. Microorganism food source hosts are selected that are known to occupy the "phytosphere" (phylloplane, phyllosphere, rhizosphere, and/or rhizoplane) of one or more crops of interest. Generally, the organism should provide stable maintenance and expression of the gene and provide for improved protection of the toxin from environmental degradation and inactivation.

A large number of microorganisms are known to inhabit the phylloplane (the surface of the plant leaves) and/or the rhizosphere (the soil surrounding plant roots) of a wide variety of important crops and are a known food source for the fire ant. These microorganisms include bacteria, algae, and fungi. Of particular interest are microorganisms, such as bacteria, e.g., genera Pseudomenas, Erwinia, Serratia, Klebsiella, Xanthomonas, Streptomyces, Rhizobium, Rhodopseudomonas, Methylophilius, Agrobacterium, Acetobacter, Lactobacillus, Arthrobacter, Azotobacter, Leuconostoc, and Alcaligenes; fungi, particularly yeast, e.g., genera Saccharomyces, Cryptococcus, Kluyveromyces, Sporobolomyces, Rhodotorula, and Aureobasidium.

Other organisms that may be used as a food source by fire ants include phytosphere bacterial species, such as: *Pseudomonas syringae, P. fluorescens, Serratia marcescens, Acetobacter xylinum, Agrobacterium tumefaciens, Rhodopseudomonas spheroides, Xanthomonas campestris, Rhizobium melioti, Alcaligenes entrophus,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae,* and *Aureobasidium pollulans.* Of particular interest are the pigmented microorganisms.

The BT strains of the present invention may be cultured using standard art media and fermentation techniques, however, certain specific conditions are disclosed herein that fall within the standard art. Upon completion of a fermentation cycle, the bacteria may be harvested by first separating the BT spores and parasporal crystals from the fermentation broth by means well known in the art. The recovered BT spores and crystals may be formulated into a wettable powder, liquid concentrate, granules, or other formulations by the addition of surfactants, dispersants, inert carriers and other components to facilitate handling and application for particular target pests.

Not generally known in the art, and specifically recognized herein, is the fact that fire ants specifically filter large objects such as bacterial spores and crystals away from the oral cavity and prevent entry of these large items into the digestive system. Therefore, it is important for fire ant solid bait preparations that particle size be limited to 0.88 microns or less, to allow the fire ant to effectively ingest the poison, but particle size is less relevant for other Hymenopteran insects. Alternatively, the BT spores and protoxin crystals can be at least partially purified and partially dissolved in a liquid, or the crystal size reduced by grinding or genetic modification, or the toxin expressed as soluble, active proteins to circumvent the size exclusion mechanism of fire ant defense.

Upon complete or partial purification, the pesticide toxin of the present invention may be provided in a concentration for the amount of liquid or dissolving liquid needed. The concentration of toxin will vary widely depending upon the nature of the particular formulation. The pesticide may be made available to fire ants at a concentration of about 1% weight to volume, however, it may be at 100% by weight if provided in a dry form with an attractant. The attractant may even be the toxin itself or a blotting agent or powder on which the toxin is provided. Dry formulations, for example, will have from about 1–95% by weight of the pesticide whereas the liquid formulations will generally be from about 1–60% by weight of the solids in the liquid phase. The formulations may be applied to the environment of the Hymenopteran pest(s), e.g., plants, soil or water, by spraying, dusting, sprinkling, baits or the like.

EXAMPLE 1

Isolation of *Bacillus Thuringiensis* Strains

A 1 gram sample of soil was mixed with 10 ml of LB buffered with 0.25 M sodium acetate, pH 6.8 and incubated with strong agitation (~200 rpm) overnight at 30° C. A 1.5 ml aliquot of the sample was removed and heat shocked at 80° C. with agitation in a 50 ml conical tube for 3 minutes. Aliquots of 10, 20 and 100 µl were then removed and plated on LB medium overnight at 30° C. The following day colonies were picked and plated onto GYS plates and incubated at 30° C. overnight. The GYS medium is prepared as follows:

| MODIFIED "GYS" MEDIUM | |
|---|---|
| | Per Liter |
| Glucose | 2.0 g |
| (NH$_4$)$_2$SO$_4$ | 2.0 g |
| CaCl$_2$ (Anhydrous) | 0.08 g |
| MgSO$_4$ (Anhydrous) | 0.20 g |
| MnSO$_4$ (Monohydrate) | 0.05 g |
| Citric Acid | 1.5 g |
| Yeast Extract | 2.0 g |
| pH may be adjusted with KOH to 7.5 and autoclaved after the desired pH is attained. | |

Isolates were examined microscopically to determine if crystalline inclusions were produced. Inclusions were visualized by staining with malachite green/Gram Safranin as follows: cells were dried onto a slide and stained for 15 minutes with a 5% aqueous solution of malachite green over boiling H$_2$O. The slide was rinsed and stained for 5–6 minutes with Gram Safranin Solution (stock solution is 2.5% solution of Safranin 0 (SIGMA™) in 100 ml ETOH; the working solution is a 1:10 dilution of stock solution in H$_2$O). The slide is rinsed and dried. Spores stain green/blue while crystals and vegetative cells stain red.

Isolates which appeared to produce crystals were noted, grown in LB overnight at 30° C. and restreaked on GYS plates to obtain axenic cultures. Cultures were inspected again by staining with Gram Safranin to identify isolates producing crystals and spores. Such cultures were grown 5 days in 7 ml of liquid GYS, stained again for crystal/spore production and centrifuged and washed 3 times w/50 ml TrisCl, pH 7.5, 10 mM KCl, and 10 mM EDTA. The pellets were lyophilized and weighed for later use.

EXAMPLE 2

Cry Toxin Preparation

To prepare toxin, one ml of culture is centrifuged in a bench-top microfuge for one minute, resuspended in 200 µl of protein solubilization buffer and boiled for 10 minutes. The prepared sample is loaded on a 12% SDS-PAGE gel and electrophoresed. The total protein profile for each sample is determined by staining of the gel with Coomassie blue. Both vegetative and sporulating cells are analyzed in this way, and an example is shown in FIG. 1. It is noted that because no protease inhibitors were used to prepare the total protein extracts, the protoxin has been entirely cleaved to the 67 kD form. In preparations where cleavage is incomplete, doublets may be seen, and in preparations where protease activity is completely prevented, a single 73 kD band is seen.

Isolates containing Cry toxin protein profiles of interest as determined by SDS-PAGE are selected for bioassay. Isolates are grown in 1-liter batch cultures containing GYS broth. After complete sporulation of the culture, determined by malachite green staining, the cultures are centrifuged and the parasporal crystals are washed using several rounds of sonification and buffer changes. The washed crystals are purified further by centrifugation on a sucrose gradient of 30–80%. The purified crystals are solubilized in a sodium carbonate buffer and the protoxin converted to activated toxin using papain or trypsin. The activated toxin is purified by HPLC or FPLC.

The purified active toxin is used in insect bioassay by adding varying concentrations to the insect diet as described above. In this way, a strain of fire ant effective BT called UTD-001 was identified. Strain UTD-001 was characterized according to its total protein banding patterns, as described above. The protein banding pattern was similar, but not identical, to the protein banding pattern of a control species—Btt as shown in FIG. 1.

Figure 2:
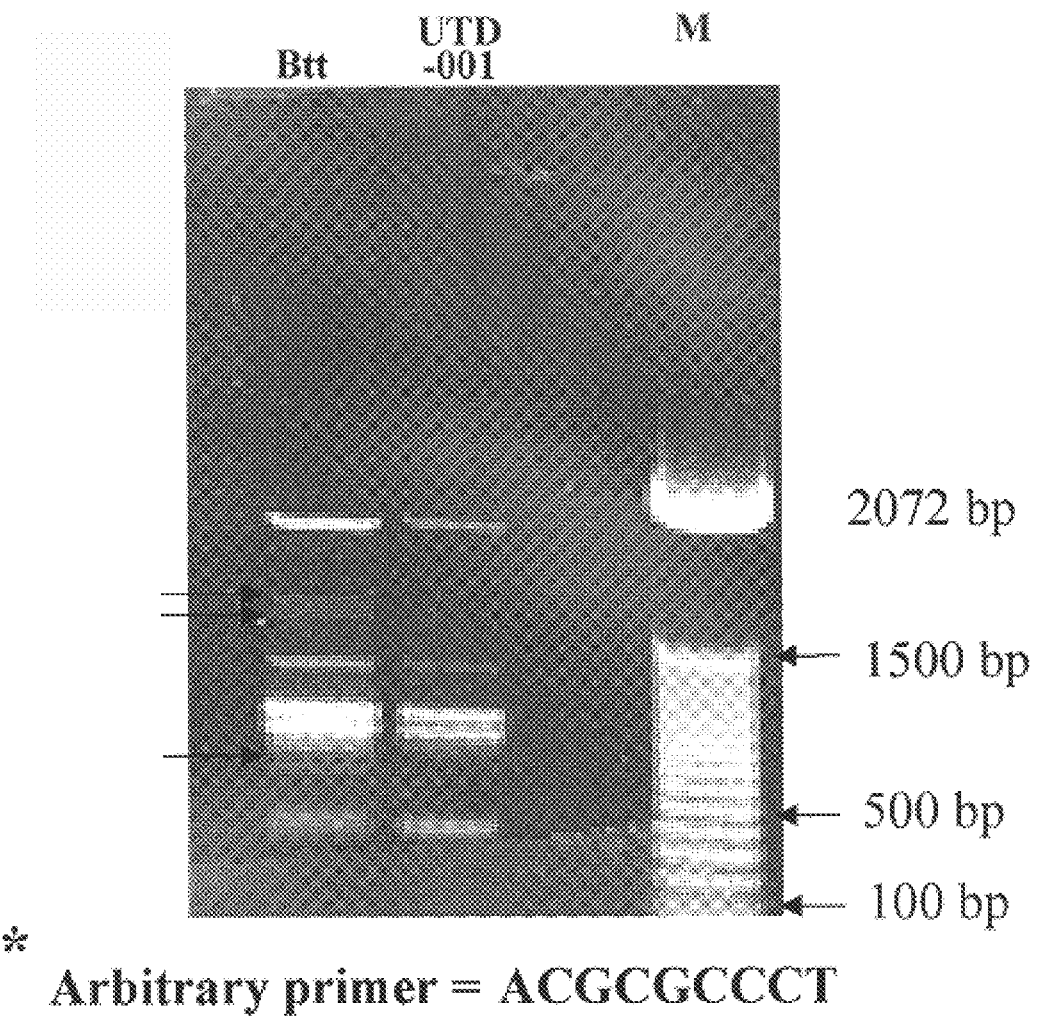
FIG. 2 is an ethidium bromide stained agarose gel of arbitrarily-primed PCR products of UTD-001 and the control species Btt. The arbitrary primer was ACGCGCCCT. The arrows indicate bands present in the Btt strain, that are absent in the UTD-001 strain. Size markers M (100 bp ladder) are indicated on the right.
Figure 3:
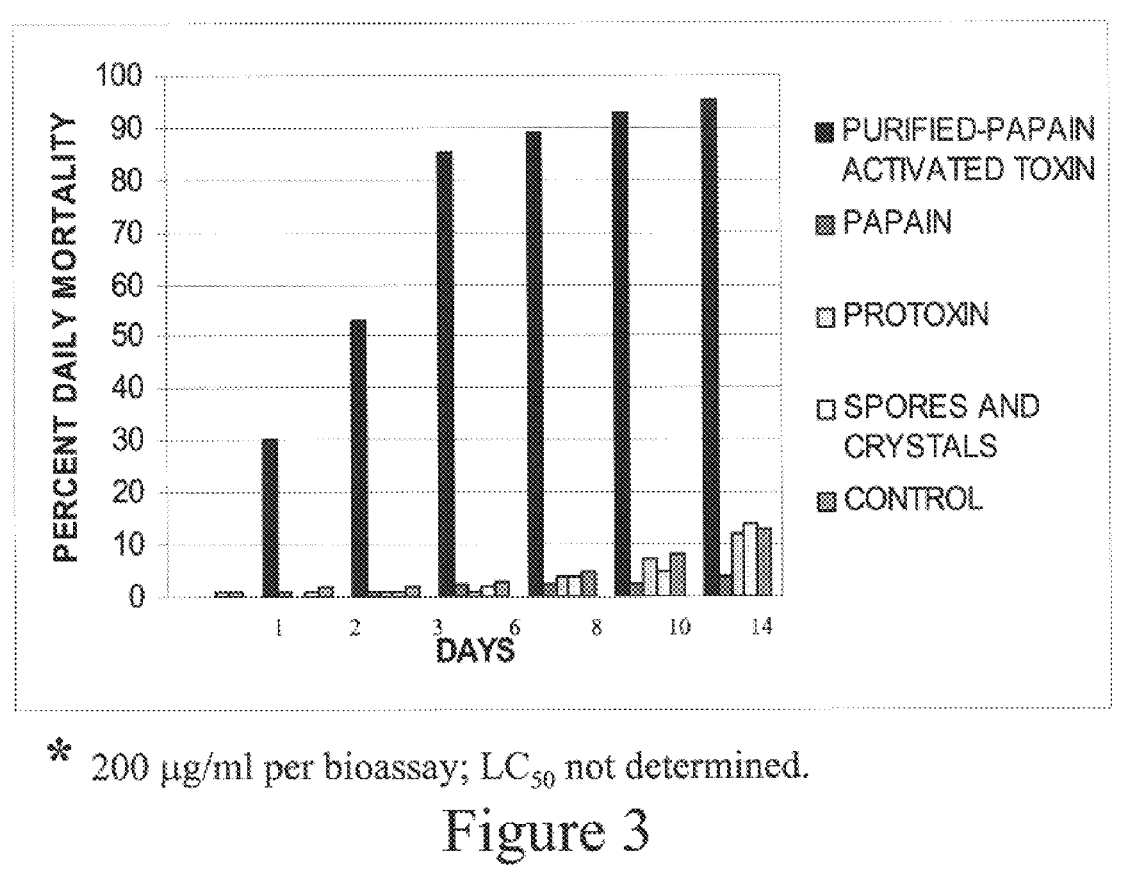
Figure 4B:
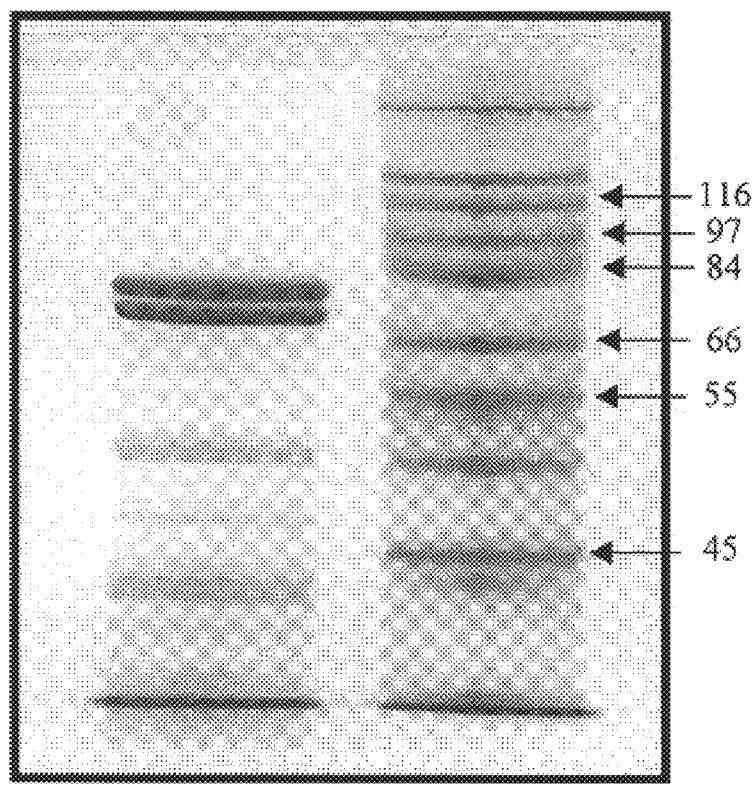

Btt is known to be effective against certain beetles, and contains a Cry3A toxin. The Cry3A toxin is expressed as an approximately 73-kD protoxin, which is activated by proteolytic cleavage to a 67 kD toxin. It should be understood to one of ordinary skill in the art that the Btt toxin exhibits toxicity properties, as illustrated in FIG. 3, for example, Cry3A-like toxins. Further characterization of the UTD strain was performed by arbitrary primer PCR (FIG. 2), a powerful method to identify BT serivars and strains, Brousseau, C., et al., (1993) Appl. Environ. Microbiol. 59: 114–119. Again, the profiles are similar but not identical to the control strain Btt. In particular, three bands (indicated by arrows) are present in the Btt strain, that are not present in the UTD-001 strain.

EXAMPLE 3

Purification and Activation of Cry Protoxin Crystals

A one-liter culture of a fire ant effective Btt strain is grown in modified GYS medium for 4–6 days until most of the cells have lysed. The medium containing the lysed cells is centrifuged for 20 minutes at 7500 rpm. The supernatant is discarded and the cell pellet transferred to 40 ml centrifuge tubes. The cell pellet is resuspended in 1M NaCl (30 ml/tube) and centrifuged for 20 minutes at 15,000 rpm. Two subsequent washes are done with distilled water. The cells (2–4 grams) are resuspended in two tubes in 68% RENOGRAFIN®-76 (20.4 ml Renografin®-76 plus a solution of 3 ml 100 mM EDTA and 6.6 ml 2% Triton X-100 in $dH_2O$) (RENOGRAFIN®-76 is diatrizoate meglumine and diatrizoate sodium manufactured by SQUIBB DIAGNOSTICS™, New Brunswick, N.J.).

The cells' debris is pelleted, for example, by centrifugation in a JA-20 or Sorvall SS-34 rotor for 2 hours at 15,000 rpm. The supernatant containing the crystals is pipetted off and placed in a separate centrifuge tube. The supernatant is filtered using 1.2-pm filter paper and, after addition of EDTA to 3–5 mM and PMSF 0.1 mg/ml, is dialyzed against distilled water for 36 hours using a dialysis membrane with a molecular weight cutoff of 12,000 to 14,000. The dialyzed material is then centrifuged for 15 min at 7,500 rpm and the supernatant containing the crystals is stored wet at 4° C.

The protoxin crystals are solubilized in 3.3 M NaBr, pH 7.0, and 50 mM phosphate buffer containing 1 mM PMSF. Insoluble papain beads (SIGMA™) are activated according to the manufacturer's instructions and added to the solubilized crystal toxin to effect cleavage. Cleavage is arrested by addition of Na-p-tosly-L-lysine chloromethyl ketone (TLCK) to 1.25 mg/ml and 0.2 volume of pH 10.0 $Na_2CO_3$. Cleaved toxin is purified by passage over Sephadex G-75 (AMERSHAM PHARMACIA BIOTECH, INC.™, Piscataway, N.J.) equilibrated with 50 mM $Na_2CO_3$, pH 10.0, containing 1 mM EDTA.

EXAMPLE 4

Alternative Method of Purification and Activation of BT Toxin

*Bacillus thuringiensis* toxin can be isolated from recombinant cells expressing Cry toxin. For example, *E. coli* containing the cry gene is prepared. A 500 ml culture is then grown to an $O.D._{600}$ of ~0.8. Where the recombinant gene is cloned under the influence of the lac promoter, expression is induced by treatment with 0.1 mM isopropyl-β-D-thiogalactopyranoside (IPTG) overnight at 37° C.

Cells are pelleted by centrifugation, for example at 5,000 rpm in a JA-14 rotor for 10 minutes. The cell pellet is resuspended in 25 ml of TES buffer (50 mM Tris, pH 8.0; 50 mM EDTA; 15% sucrose). Cells are lysed by treatment with lysozyme (0.5 mg/ml final concentration) and PMSF (0.1 mM final concentration) for 30 minutes at room temperature followed by sonication, 3×1 minute on ice. The supernatant and surface debris are discarded and the cells are suspended in 20 ml TTN buffer (20 mM Tris, pH 8.0; 2% Triton X-100; 0.5 M NaCl). The pellets are first suspended with a spatula, then with a glass Dounce, and then pelleted at 12,000 rpm for 15 minutes. This washing procedure is repeated for 4 cycles. The pellet is then washed 2× with 20 ml PBS: Acetone (5:1) as above followed by a wash in PBS (per liter: 8 gm NaCl; 0.2 gm KCl; 1.44 gm $Na_2HPO_4$; 0.24 grm $KH_2PO_4$) alone. Finally, the pellet is resuspended in 20 ml of $Na_2CO_3$ buffer (50 mM $Na_2CO_3$, pH 10.0; 5 mM DTT) and can be stored at 4° C. or is shaken at 37° C. for 4 hours to solubilize the protoxin. The resulting milky solution is pelleted to remove insoluble material, and additional sodium carbonate may be added if desired.

The protoxin preparation can be analyzed on a mini-gel and should show a predominantly 73-kD protoxin plus some smaller (bacterial) proteins. Protein can be quantified using the BCA protein reagent (PIERCE™) as per the manufacturer's recommendations prior to papain treatment. Protoxin is stored at 4° C. Freezing results in deterioration of the protoxin.

Activation of the protoxin can alternatively be performed using trypsin. TPCK (SIGMA™) trypsin is added for a trypsin:protoxin ratio of 1:20 and the mixture is shaken at room temperature for 15 minutes. The reaction mixture is placed on ice and an aliquot is checked for complete digestion on a mini-gel. If digestion is complete, PMSF is added to 100 μM on ice.

The cleaved mixture is dialyzed overnight against 20 mM Tris with 100 mM NaCl, pH 9.5. Prior to final dialysis, concentration of activated toxin should be no more than 2 mg/ml to avoid precipitation. The dialyzed preparation is filtered through a 0.2 μm filter and subjected to further purification by FPLC. The 18% B fraction on FPLC is collected using a 100–1000 mM NaCl gradient as described below.

EXAMPLE 5

Purification of Cry Toxin by FPLC

FPLC procedures are conducted according to standard procedures including the following particulars.

Typical FPLC Profile (With HR5 Column at Port 3, with 1 ML Sample Loop):

| | | | |
|---|---|---|---|
| 0.0 | CONC %B | 0.0 | (initial buffer is 100% A) |
| 0.0 | ML/MIN | 1.0 | (buffer flow rate) |
| 0.0 | CM/MIN | 0.5 | (chart speed as controlled by computer) |
| 0.0 | PORT.SET | 6.0 | (sampler "off") |
| 0.0 | VALVE.POS | 1.1 | (valve #1 bypass loop) |
| 0.0 | VALVE.POS | 2.3 | (valve #2 leading to column at port 3) |
| 0.0 | VALVE.POS | 3.3 | (valve #3 leading from column at port 3) |
| 0.0 | MIN/MARK | 110 | N/A |
| 0.5 | VALVE.POS | 1.2 | (valve #1 open, loads loop onto column) |
| 2.0 | VALVE.POS | 1.1 | (valve #1 closes after entire column has loaded on column, plus extra) |
| 7.0 | CONC %B | 0.0 | (provides 5 minutes of Buffer A for flow-through) |
| 37. | CONC %B | 30. | (standard gradient of 1%/min) |
| 40. | CONC %B | 100 | (at 30% B gradient then jumps to 100% in 3 minutes) |
| 45. | CONC %B | 100 | (5 minutes hold at 100% B) |
| 45. | CONC %B | 0.0 | (jump to 100% A) |
| 60. | CONC %B | 0.0 | (end of method after 5 minute hold at 100% A) |

FPLC Buffer 'A' (low salt): 50 mM Tris pH 10.0
100 mM NaCl
5% glycerol; filter through 0.2 μm filter.
FPLC Buffer 'B' (high salt): 50 mM Tris pH 10.0
1-M NaCl
5% glycerol; filter through 0.2 μm filter.

EXAMPLE 6

Fire Ant Mortality

The invention described herein was targeted toward the identification of BT effective in killing populations of the imported fire ant. Consideration was given to BT toxin characteristics together with the characteristics of the gut environment in which the toxin must exert its toxic effect. Some BT strains produce toxins that work at neutral pH and lower (pH range of 5–7). The gut environments of different insects may be characterized by different pH's. In particular, the gut of fire ants is slightly acidic. A BT toxin that is effective against fire ants must survive in the fire ant gut environment.

FIG. 3 is a graph showing the mortality of the populations of the imported fire ant that were treated with various BT toxin concentrations. Briefly, the procedure is as follows. A separate colony of worker ants is used for testing each concentration. The various concentrations are combined in a 10% solution of sucrose in distilled water for all of the tests. Prior to the test, the worker ant colonies are held without food for 5 days. Then the 20 workers for each repetition are placed in 30-ml cups for 14 days. The toxin preparations are placed in cups for only the initial 24 hours after that, they are removed and replaced with a 10% sucrose in distilled water solution. Percent mortality is recorded at day 1, 2, 3, 6, 8, 10 and 14. The control is 10% sucrose in distilled water solution only.

$LC_{50}$ has not yet been conclusively determined, but preliminary results from 6 month old toxin of doubtful quality indicates that the $LC_{50}$ could be as low as 70 ng/ml. Studies are also planned to determine the species specificity of the new Cry toxin. In particular, bees and wasps will be assayed for toxin efficacy.

EXAMPLE 7

Cloning of the Cry Gene from UTD-001

Figure 5:
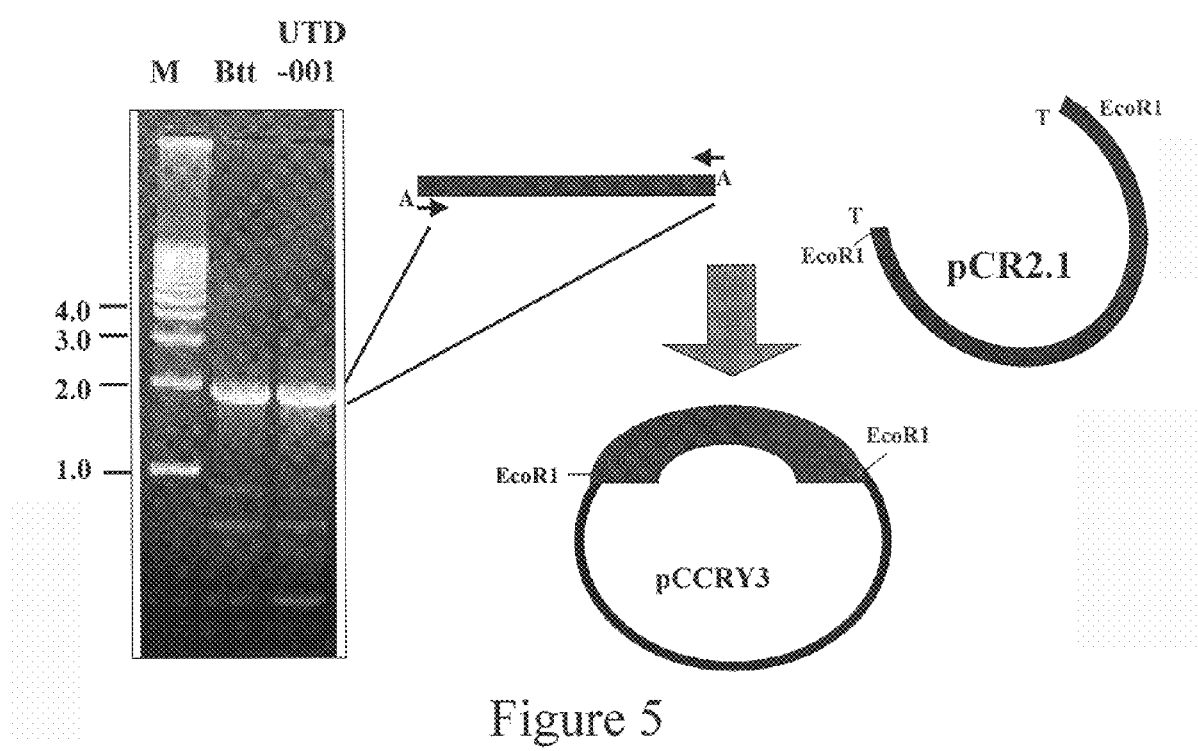
FIG. 5 illustrates the cloning of the Cry toxin gene from a 1.8 kb PCR product of UTD-001 into the TA cloning vector pCR2.1 (INVITROGEN™) to produce the pCCRY3 plasmid. Primers used were Forward: ATGAATCCGAA-CAATCGAAG (SEQ. ID. NO: 3) and Reverse: TTAAT-TCACTGGAATAAATTC (SEQ. ID. NO: 4)

The cry gene of strain UTD-001 are contained on plasmids of similar size and restriction pattern as that shown by the control strain Btt (not shown). Hence, it is anticipated that the gene might be very similar to the Btt gene. Thus, primers cry3A-F and cry3A-R (derived from the Btt cry gene) were used to amplify a 1.8-kb fragment of UTD-001 that has a TAQ created A overhang. The fragment is excised from a low-melt agarose gel and ligated into linearized pCR2.1 with a T overhang to produce the pCRRY3 plasmid (see FIG. 5—TA cloning method by INVITROGEN™).

The gene was sequenced and is shown in FIG. 6 along with the conceptually translated protoxin amino acid sequence in FIG. 7. The coding region extends from nucleotides 56 or 58 to the end. The putative proteolytic cleavage site is indicated by the arrow and the toxin sequence is indicated in bold. The calculated molecular weight of the protoxin is 72.9 kD, and the toxin is about 67 kD, which agrees well with the sizes as determined by SDS-PAGE.

The gene shows greatest homology (98%) to the Cry3A gene of the Btt strain used as a control. In particular, the amino acid sequence (SEQ ID NO: 2) was Searched by BLASTP under the search parameters described under definitions above and homologies to a number of Coleoptera specific, 73–74 Kd Cry protoxins were found. The closest homology was to the Cry3A(A) toxin (Acc. No. P07130) from *B. thuringiensis* var. *tenebrionis* with homologies ranging from 632/644 (98%) to 572/584 (97%) amino acid identities from varying Btt isolates. The next closest homologies were to the Cry3C(A) toxin of *B. thuringiensis* subsp. *kurstaki* (Acc. No. Q45744) at 479/652 (73%) amino acid identities, and the Cry3B(B) toxin (Acc. No. Q06117) with 439/650 (67%) identities. Similarly, the nucleotide sequence showed 1902/1936 (98%) nucleotide homology to the Cry3A(A) sequence of Btt.

Because the novel cry toxin was surprisingly closely related to Btt toxin, a toxin known to only be effective against Coleoptera, the Btt toxin was also tested for efficacy against fire ants. Preliminary results indicate that the Btt toxin is effective against the fire ant, although with less efficacy than the strain described herein. Thus, a new use for the prior Btt toxin has been unexpectedly discovered. This fire ant activity may have been previously obscured because of the unusual dietary requirements of the fire ant, which cannot consume large solids.

All references cited herein are hereby incorporated by reference. Although this invention has been described in reference to illustrative embodiments, this description is not intended to be construed in a limiting sense. Various modifications and combinations of the illustrative embodiments, as well as other embodiments of the invention, will be apparent to persons skilled in the art upon reference to the description. It is, therefore, intended that the appended claims encompass any such modifications or embodiments.

What is claimed is:

1. An isolated or recombinant nucleic acid molecule, comprising a nucleotide sequence encoding a protein toxic to Formicidae which protein comprises residues 58 to 644 of SEQ ID NO: 2.

2. The nucleic acid molecule of claim 1, wherein the nucleotide sequence encodes a precursor to a protein toxic to Formicidae which precursor comprises SEQ ID NO: 2.

3. The nucleic acid molecule of claim 2, comprising a nucleotide sequence of nucleotides 1 to 1936 of SEQ ID NO: 1.

4. The nucleic acid molecule of claim 1, comprising a nucleotide sequence of at least nucleotides 174 to 1936 of SEQ ID NO: 1.

5. A nucleic acid molecule which comprises an expression system for expressing the nucleotide sequence of claim 4.

6. Host cells modified to contain the nucleic acid molecule of claim 5.

7. A method to produce a protein encoded by a nucleotide sequence comprising nucleotides 174–1936 of SEQ. ID. NO: 1, which method comprises culturing the cells of claim 6 so as to produce said protein.

8. A nucleic acid molecule which comprises an expression system for expression of the nucleotide sequence of claim 1 in a host cell.

9. A host cell which contains the nucleic acid molecule of claim 8.

10. A method to produce a protein comprising residues 58–644 of SEQ. ID. NO: 2, which method comprises culturing the cells of claim 9 so as to produce said protein.

11. A nucleic acid molecule, comprising a nucleotide sequence encoding a protein at least 99% homologous over the entire length of residues 58 to 644 of SEQ ID NO: 2, wherein said protein is toxic to Formicidae.

12. A nucleic acid molecule which comprises an expression system for expressing the nucleotide sequence of claim 11.

13. Host cells modified to contain the nucleic acid molecule of claim 12.

14. A method to produce a protein at least 99% homologous over the entire length of residues 58 to 644 of SEQ ID NO: 2, wherein said protein is toxic to Formicidae, which method comprises culturing the cells of claim 13 so as to produce said protein.

* * * * *

SEQUENCE LISTING

<160> NUMBER OF SEQ ID NOS: 4

<210> SEQ ID NO 1
<211> LENGTH: 1936
<212> TYPE: DNA
<213> ORGANISM: Bacillus thuringiensis

<400> SEQUENCE: 1

```
atgaatccga acaatcgaag tgaacatgat acaataaaaa ctactgaaaa taatgaggtg     60
ccaactaacc atgttcaata tcctttagcg gaaactccaa atccaacact agaagattta    120
aattataaag agtttttaag aatgactgca gataataata cggaagcact agatagctct    180
acaacaaaag atgtcattca aaaaggcatt tccgtagtag gtgatctcct aggcgtagta    240
ggtttcccgt ttggtggagc gcttgtttcg ttttatacaa actttttaaa tactatttgg    300
ccaagtgaag acccgtggaa ggcttttatg gaacaagtag aagcattgat ggatcagaaa    360
atagctgatt atgcaaaaaa taaagctctt gcagagttac agggccttca aaataatgtc    420
gaagattatg tgagtgcatt gagttcatgg caaaaaaatc ctgtgagttc acgaaatcca    480
catagccagg ggcggataag agagctgttt tctcaagcag aaagtcattt tcgtaattca    540
atgccttcgt ttgcaatttc tggatacgag gttctatttc taacaacata tgcacaagct    600
gccaacacac atttattttt actaaaagac gctcaaattt atggagaaga atggggatac    660
aaaaaagaag atattgctga atttttaaaa agacaactaa aacttaccca ggaatatact    720
gaccattttg ttcaatggta ttatgttgga ttagataaaa ttagaggttc attctatgaa    780
tcttgggtaa actttaaccg ttatcgcaga gagatgacat taacagtatt agatttaatt    840
gcactatttc cattgtatga tgttcggcta tacccaaaag aagttaaaac cgaattaaca    900
agagacgttt taacagatcc aattgtcgga gtcaacaacc ttaggggcta tggaacaacc    960
ttctctaata tagaaaatta tattcgaaaa ccacatctat ttgactatct gcatagaatt   1020
caatttcaca cgcggttcca accaggatat tatggaaatg actctttcaa ttattggtcc   1080
ggtaattatg tttcaactag accaagcata ggatcaaatg atataatcac atctccattc   1140
tatggaaata aatccagtga acctgtacaa aatttaggat ttaatggaga aaaagtctat   1200
agagccgtag caaatacaaa tcttgcggtc tggccgtccg ctgtaaattc aggtgtaaca   1260
aaagtgaaat ttagccaata taatgatcaa acagatgaag caagtacaca aacgtcggac   1320
tcaaaaagaa atgttggcgc ggtcagctgg gattctatcg atcaattgcc tccagaagca   1380
acagatgaac ctctagaaaa gggatatagc catcaactca attatgtaat gtgcttttta   1440
atgcagggta gtagaggaac aatcccagtg ttaacttgga cacataaaag tgtagacttt   1500
tttaacatga ttgattcgaa aaaaattaca caacttccgt tagtaaaggc atataagtta   1560
caatctggtg cttccgttgt cgcaggtcct aggtttacag gaggagatat cattcaatgc   1620
acagaaaatg gaagtgcggc aactatttac gttacaccgg atgtgtcgta ctctcaaaaa   1680
tatcgagcta gaattcatta tgcttctaca tctcagataa catttacact cagtttagac   1740
ggggcaccat ttaatcaata ctatttcgat aaaacgataa ataaaggaga cacattaacg   1800
tataattcat ttaatttagc aagtttcagc acaccattcg aattatcagg gaataactta   1860
caaataggcg tcacaggatt aagtgctgga gataaagttt atatagacaa aattgaattt   1920
attccagtga attaaa                                                    1936
```

```
<210> SEQ ID NO 2
<211> LENGTH: 644
<212> TYPE: PRT
<213> ORGANISM: Bacillus thuringiensis

<400> SEQUENCE: 2

Met Asn Pro Asn Asn Arg Ser Glu His Asp Thr Ile Lys Thr Thr Glu
 1               5                  10                  15

Asn Asn Glu Val Pro Thr Asn His Val Gln Tyr Pro Leu Ala Glu Thr
            20                  25                  30

Pro Asn Pro Thr Leu Glu Asp Leu Asn Tyr Lys Glu Phe Leu Arg Met
        35                  40                  45

Thr Ala Asp Asn Asn Thr Glu Ala Leu Asp Ser Ser Thr Thr Lys Asp
 50                  55                  60

Val Ile Gln Lys Gly Ile Ser Val Val Gly Asp Leu Leu Gly Val Val
 65                  70                  75                  80

Gly Phe Pro Phe Gly Gly Ala Leu Val Ser Phe Tyr Thr Asn Phe Leu
                85                  90                  95

Asn Thr Ile Trp Pro Ser Glu Asp Pro Trp Lys Ala Phe Met Glu Gln
                100                 105                 110

Val Glu Ala Leu Met Asp Gln Lys Ile Ala Asp Tyr Ala Lys Asn Lys
            115                 120                 125

Ala Leu Ala Glu Leu Gln Gly Leu Gln Asn Asn Val Glu Asp Tyr Val
130                 135                 140

Ser Ala Leu Ser Ser Trp Gln Lys Asn Pro Val Ser Ser Arg Asn Pro
145                 150                 155                 160

His Ser Gln Gly Arg Ile Arg Glu Leu Phe Ser Gln Ala Glu Ser His
                165                 170                 175

Phe Arg Asn Ser Met Pro Ser Phe Ala Ile Ser Gly Tyr Glu Val Leu
                180                 185                 190

Phe Leu Thr Thr Tyr Ala Gln Ala Ala Asn Thr His Leu Phe Leu Leu
            195                 200                 205

Lys Asp Ala Gln Ile Tyr Gly Glu Glu Trp Gly Tyr Lys Lys Glu Asp
210                 215                 220

Ile Ala Glu Phe Leu Lys Arg Gln Leu Lys Leu Thr Gln Glu Tyr Thr
225                 230                 235                 240

Asp His Phe Val Gln Trp Tyr Tyr Val Gly Leu Asp Lys Ile Arg Gly
                245                 250                 255

Ser Phe Tyr Glu Ser Trp Val Asn Phe Asn Arg Tyr Arg Arg Glu Met
                260                 265                 270

Thr Leu Thr Val Leu Asp Leu Ile Ala Leu Phe Pro Leu Tyr Asp Val
            275                 280                 285

Arg Leu Tyr Pro Lys Glu Val Lys Thr Glu Leu Thr Arg Asp Val Leu
290                 295                 300

Thr Asp Pro Ile Val Gly Val Asn Asn Leu Arg Gly Tyr Gly Thr Thr
305                 310                 315                 320

Phe Ser Asn Ile Glu Asn Tyr Ile Arg Lys Pro His Leu Phe Asp Tyr
                325                 330                 335

Leu His Arg Ile Gln Phe His Thr Arg Phe Gln Pro Gly Tyr Tyr Gly
                340                 345                 350
```

-continued

```
Asn Asp Ser Phe Asn Tyr Trp Ser Gly Asn Tyr Val Ser Thr Arg Pro
        355                 360                 365

Ser Ile Gly Ser Asn Asp Ile Ile Thr Ser Pro Phe Tyr Gly Asn Lys
    370                 375                 380

Ser Ser Glu Pro Val Gln Asn Leu Gly Phe Asn Gly Glu Lys Val Tyr
385                 390                 395                 400

Arg Ala Val Ala Asn Thr Asn Leu Ala Val Trp Pro Ser Ala Val Asn
                405                 410                 415

Ser Gly Val Thr Lys Val Lys Phe Ser Gln Tyr Asn Asp Gln Thr Asp
            420                 425                 430

Glu Ala Ser Thr Gln Thr Ser Asp Ser Lys Arg Asn Val Gly Ala Val
        435                 440                 445

Ser Trp Asp Ser Ile Asp Gln Leu Pro Pro Glu Ala Thr Asp Glu Pro
    450                 455                 460

Leu Glu Lys Gly Tyr Ser His Gln Leu Asn Tyr Val Met Cys Phe Leu
465                 470                 475                 480

Met Gln Gly Ser Arg Gly Thr Ile Pro Val Leu Thr Trp Thr His Lys
                485                 490                 495

Ser Val Asp Phe Phe Asn Met Ile Asp Ser Lys Lys Ile Thr Gln Leu
            500                 505                 510

Pro Leu Val Lys Ala Tyr Lys Leu Gln Ser Gly Ala Ser Val Val Ala
        515                 520                 525

Gly Pro Arg Phe Thr Gly Gly Asp Ile Ile Gln Cys Thr Glu Asn Gly
    530                 535                 540

Ser Ala Ala Thr Ile Tyr Val Thr Pro Asp Val Ser Tyr Ser Gln Lys
545                 550                 555                 560

Tyr Arg Ala Arg Ile His Tyr Ala Ser Thr Ser Gln Ile Thr Phe Thr
                565                 570                 575

Leu Ser Leu Asp Gly Ala Pro Phe Asn Gln Tyr Tyr Phe Asp Lys Thr
            580                 585                 590

Ile Asn Lys Gly Asp Thr Leu Thr Tyr Asn Ser Phe Asn Leu Ala Ser
        595                 600                 605

Phe Ser Thr Pro Phe Glu Leu Ser Gly Asn Asn Leu Gln Ile Gly Val
    610                 615                 620

Thr Gly Leu Ser Ala Gly Asp Lys Val Tyr Ile Asp Lys Ile Glu Phe
625                 630                 635                 640

Ile Pro Val Asn

<210> SEQ ID NO 3
<211> LENGTH: 20
<212> TYPE: DNA
<213> ORGANISM: Bacillus thuringiensis

<400> SEQUENCE: 3
atgaatccga acaatcgaag                                                   20

<210> SEQ ID NO 4
<211> LENGTH: 21
<212> TYPE: DNA
<213> ORGANISM: Bacillus thuringiensis

<400> SEQUENCE: 4
ttaattcact ggaataaatt c                                                 21
```